(12) United States Patent
Fischbach et al.

(10) Patent No.: US 7,747,321 B2
(45) Date of Patent: Jun. 29, 2010

(54) IMPLANTABLE MEDICAL DEVICE FEEDTHROUGH ASSEMBLY HAVING A COATED CONDUCTOR

(75) Inventors: Adam C. Fischbach, Inver Grove Heights, MN (US); Steve L. Fedor, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 28 days.

(21) Appl. No.: 12/015,960

(22) Filed: Jan. 17, 2008

(65) Prior Publication Data

US 2008/0114413 A1    May 15, 2008

Related U.S. Application Data

(63) Continuation of application No. 11/148,538, filed on Jun. 9, 2005, now Pat. No. 7,340,305.

(51) Int. Cl.
*A61N 1/375* (2006.01)
(52) U.S. Cl. .......................................... 607/36; 607/37
(58) Field of Classification Search ........................ None
See application file for complete search history.

(56) References Cited

U.S. PATENT DOCUMENTS

| 4,514,589 | A | 4/1985 | Aldinger et al. |
| 4,940,858 | A | 7/1990 | Taylor et al. |
| 5,072,873 | A | 12/1991 | Liu et al. |
| 5,366,496 | A | 11/1994 | Dahl et al. |
| 5,370,663 | A | 12/1994 | Lin |
| 5,406,444 | A | 4/1995 | Selfried et al. |
| 5,531,003 | A | 7/1996 | Seifried et al. |
| 5,662,696 | A | 9/1997 | Kroll et al. |
| 6,169,925 | B1 | 1/2001 | Villaseca et al. |
| 6,765,779 | B2 * | 7/2004 | Stevenson et al. ............ 361/302 |
| 6,765,780 | B2 * | 7/2004 | Brendel et al. ............... 361/302 |
| 6,852,925 | B2 | 2/2005 | Wolf et al. |
| 6,888,715 | B2 * | 5/2005 | Stevenson et al. ............ 361/302 |
| 6,999,818 | B2 * | 2/2006 | Stevenson et al. .............. 607/37 |
| 7,038,900 | B2 * | 5/2006 | Stevenson et al. ............ 361/302 |
| 2003/0179536 | A1 * | 9/2003 | Stevenson et al. ............ 361/302 |
| 2003/0213605 | A1 * | 11/2003 | Brendel et al. ............. 174/35 R |
| 2004/0257747 | A1 * | 12/2004 | Stevenson et al. ............ 361/302 |
| 2005/0060003 | A1 | 3/2005 | Taylor et al. |
| 2006/0259093 | A1 * | 11/2006 | Stevenson et al. .............. 607/37 |

* cited by examiner

*Primary Examiner*—Carl H. Layno
*Assistant Examiner*—Jon-Eric C. Morlaes
(74) *Attorney, Agent, or Firm*—Faegre & Benson LLP

(57) ABSTRACT

An electrical feedthrough for an implantable medical device (IMD) is provided that employs a feedthrough conductor having a non-platinum based inner core and one or more layers of a conductive coating to control oxide growth on the surface of the conductor. The coating permits soldering the feedthrough conductor to IMD electronics. The resulting feedthrough provides a substantial cost savings over feedthroughs employing a solid platinum or platinum-iridium conductor.

15 Claims, 5 Drawing Sheets

IMPLANTABLE MEDICAL DEVICE FEEDTHROUGH ASSEMBLY HAVING A COATED CONDUCTOR

CROSS REFERENCE TO RELATED APPLICATION

This application is a continuation of U.S. patent application Ser. No. 11/148,538 filed Jun. 9, 2005, entitled "IMPLANTABLE MEDICAL DEVICE FEEDTHROUGH ASSEMBLY HAVING A COATED CONDUCTOR" now U.S. Pat. No. 7,340,305 which is incorporated herein by reference in its entirety.

TECHNICAL FIELD

The present invention relates to feedthroughs for use in implantable medical devices. More specifically, the invention relates to feedthrough designs having multi-layer feedthrough conductors.

BACKGROUND

Electrical feedthroughs are used in implantable medical devices (IMDs) such as cardiac rhythm management devices (e.g., pacemakers and implantable cardioverter/defibrillators) to electrically connect electronic circuitry contained in a hermetically-sealed housing to external components such as, for example, therapy leads. Such feedthroughs include one or more conductive elements that extend into the hermetically-sealed interior of the device housing where they are electrically connected to the IMD electronic components (e.g., control circuitry or battery), through an insulating material, and outside the IMD, where they are electrically connected to therapy lead terminals. Electrical feedthroughs for implantable medical devices may also incorporate filters for filtering electromagnetic interference (EMI) that could impair the performance of the other IMD electronics.

The feedthrough may contact body fluids after implantation. Accordingly, feedthroughs are typically constructed of biocompatible materials. Platinum and platinum-iridium alloys are commonly-used as feedthrough conductor materials because they are biocompatible. Because of the high cost of platinum, however, it is desirable to identify alternative feedthrough conductor materials and configurations.

Other biocompatible conductive materials such as tantalum and niobium and their alloys are susceptible to surface oxide growth, which is encouraged by various high temperature processes (e.g., brazing) the conductor undergoes during fabrication of the feedthrough. The oxide layer impairs the electrical connections between the feedthrough conductor and the IMD electronic components, including the EMI filters when used, to which it is connected. Furthermore, the oxide layer limits the available methods of establishing that electrical connection. In particular, this oxide layer hinders electrically connecting the feedthrough and the IMD electronic component by soldering the feedthrough conductor to a terminal or port on the electronic component. In some cases, however, it may be especially desirable, from a manufacturing standpoint, to solder the feedthrough conductor to the IMD electronic components.

U.S. Pat. No. 5,531,003, issued to Selfried et. al., teaches a feedthrough utilizing a tantalum or niobium terminal pin coated with a thin film of a conductive metal, e.g., platinum, to reduce the insulating effect of the oxide layer on the tantalum or niobium pin. As taught therein, the coating "must not be too thick" so as to prevent the glass insulating material used to seal the terminal pin into the feedthrough from "seeing" the tantalum or niobium terminal pin and not just the coating. The '003 patent specifically teaches that a coating thickness of 10,000 angstroms (1 micron) or less is satisfactory. It has been found, however, that with coatings this thin on tantalum or niobium terminal pins, the resulting feedthrough conductor cannot be readily soldered to provide a robust electrical connection to the IMD internal electronic devices after the aforementioned high temperature processes are performed. One possible explanation for this is that with such thin coatings, the tantalum or niobium terminal pin material migrates to the surface of the coating during the high-temperature processes such as brazing. As a result of this migration, an oxide layer may form on the surface of the coating, thus inhibiting the solderability of the terminal pin.

Accordingly, there is a need in the art for an implantable medical device feedthrough utilizing a conductor design that is inexpensive, but which also permits the conductor to be soldered to the IMD electronic circuitry.

SUMMARY

The present invention, according to one embodiment, is an implantable medical device for delivering a therapy. The device includes a hermetically-sealed housing enclosing an electronic component, a header coupled to the housing and adapted to receive a terminal pin of a therapy lead, and a feedthrough coupled to the housing. The feedthrough includes a ferrule that mates with an opening in the housing, an insulating material, and a conductor coupled to the electronic component inside the housing by a soldered joint. The conductor includes a conductive metal core and an oxide-resistant coating.

The present invention, according to another embodiment, is a feedthrough for use in an implantable medical device having a hermetically-sealed housing, a header coupled to the housing and adapted to receive a therapy lead, and a printed circuit board located within the housing. The feedthrough includes an annular ferrule adapted to mate with an opening in the housing, an insulating material disposed within and coupled to the ferrule, and a conductor extending through the insulating material. The conductor has a proximal portion disposed within the header and a distal portion within the housing, and includes a conductive inner core and an oxide-resistant cladding with a thickness of at least about 2.0 microns.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
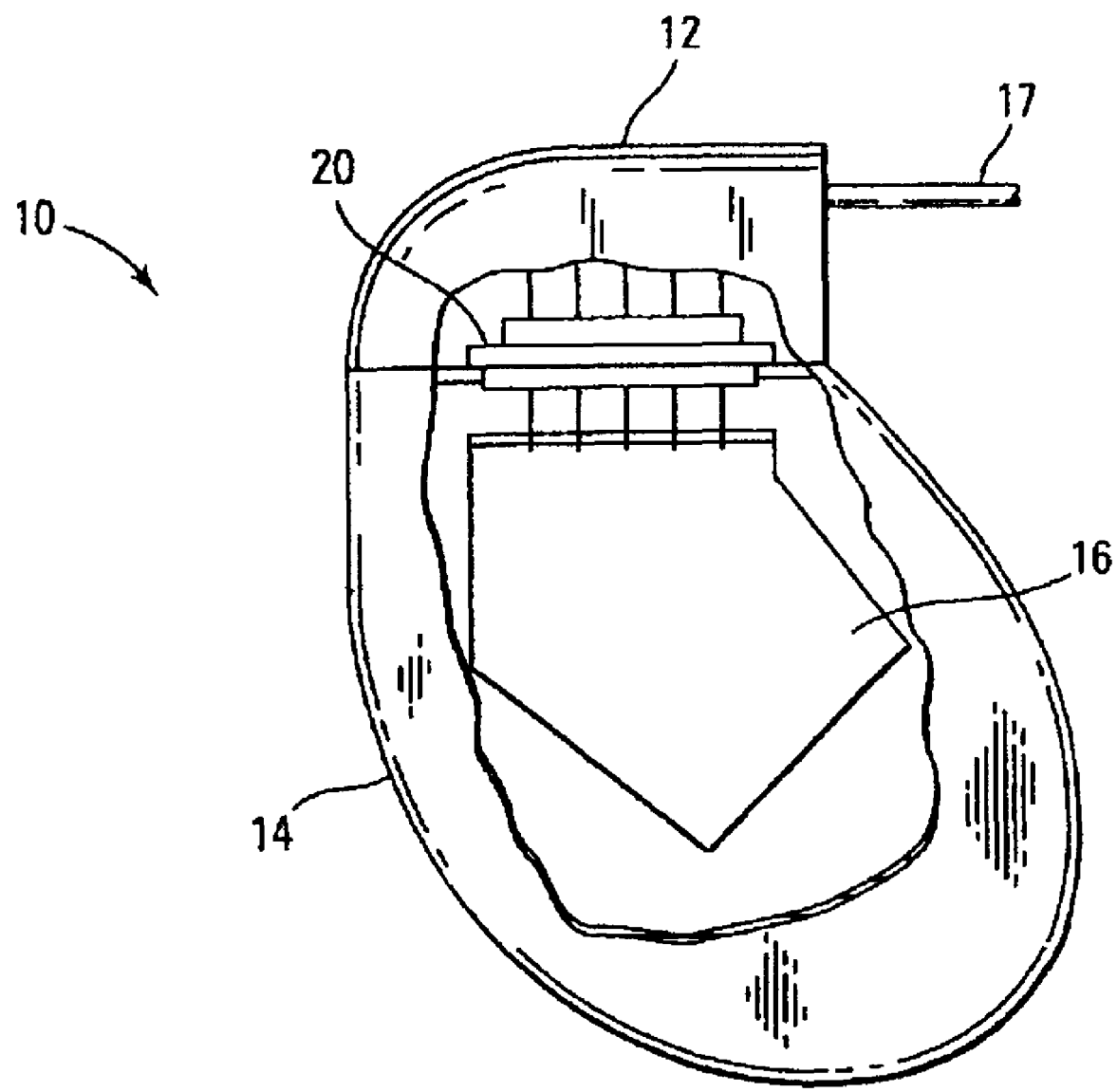
FIG. 1 is a schematic cutaway view of an implantable medical device employing a feedthrough according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a schematic cutaway view of an implantable medical device 10 incorporating a feedthrough according to one embodiment of the present invention. As shown in FIG. 1, the IMD 10 includes a header 12, a housing 14, one or more electronic components such as a printed circuit board (PCB) 16, one or more external components such as a therapy lead 17, and a feedthrough 20. The PCB 16 is disposed within the hermetically sealed interior of the housing 14. The feedthrough 20 is coupled to the housing 14 and extends partially within the housing 14 and partially outside the housing 14.

The header 12 encapsulates the portion of the feedthrough 14 that extends externally to the housing 14, and it operates to operatively couple a terminal block on a distal end of the therapy lead 17 to the feedthrough 20 (for simplicity, this coupling is not shown). The PCB 16 is adapted to electrically couple with the portion of the feedthrough 20 that extends within the housing 14. Thus, during operation of the IMD 10, the PCB 16 can communicate electrically with an electrode (not shown) at the distal end of the therapy lead 17, by way of the feedthrough 20.

Figure 2:
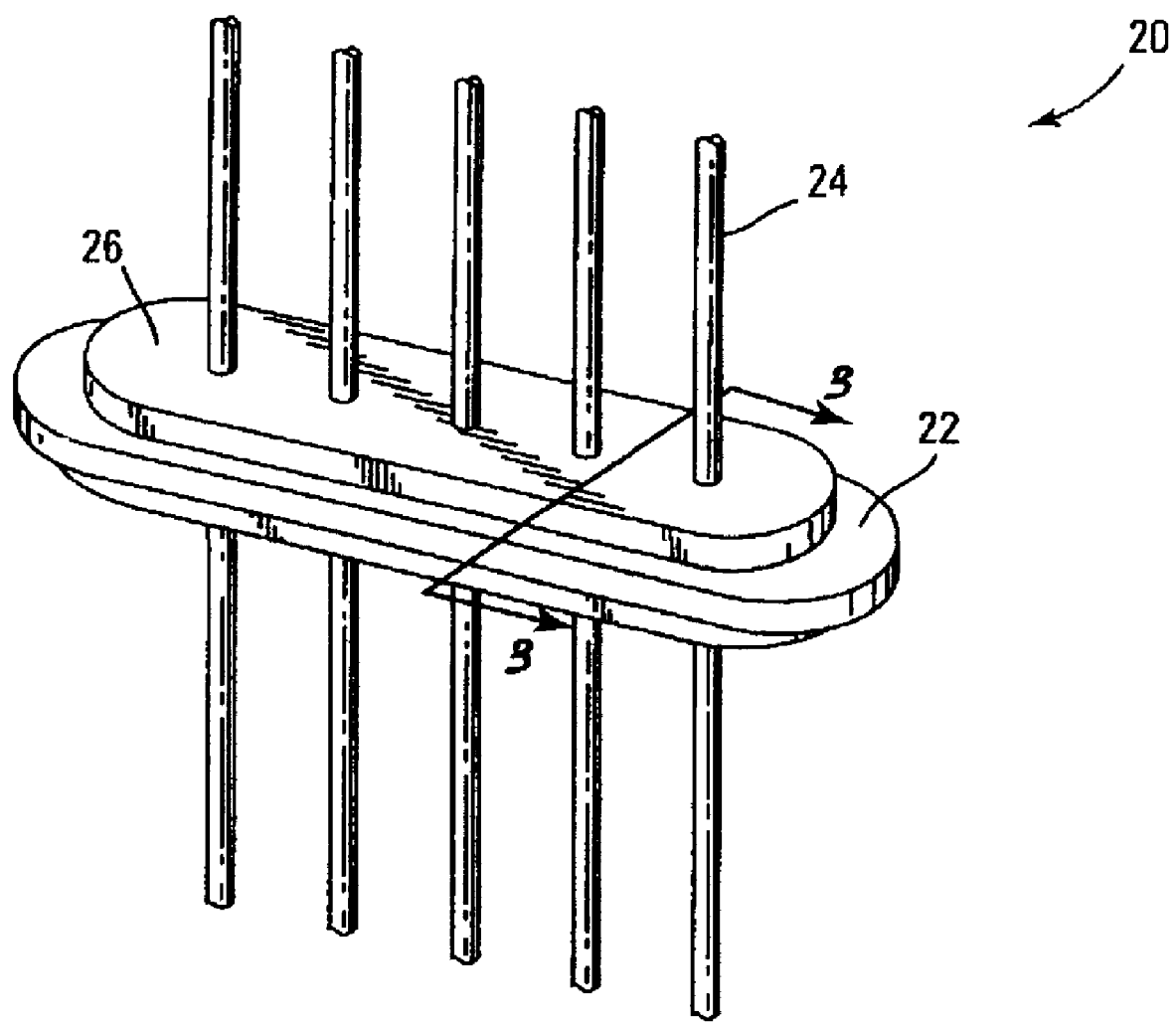
FIG. 2 is a perspective view of an exemplary feedthrough for use in an implantable medical device according to one embodiment of the present invention.

FIG. 2 shows a perspective view of a feedthrough 20 according to one embodiment of the present invention. As shown in FIG. 2, the feedthrough 20 includes a ferrule 22, one or more feedthrough conductors 24, and an insulator 26. FIG. 2 depicts an embodiment having a plurality of conductors 24, although other embodiments may employ more or fewer conductors. In one embodiment, the feedthrough 20 includes a single conductor 24. The ferrule 22 has a size and shape adapted to mate with an opening in the housing 14 (see FIG. 1). The conductors 24 extend through the insulator 26, which is disposed within the ferrule 22, from inside the housing 14 to outside the housing 14. The insulator 26 operates to electrically isolate the feedthrough conductor 24 from the ferrule 22.

Figure 3:
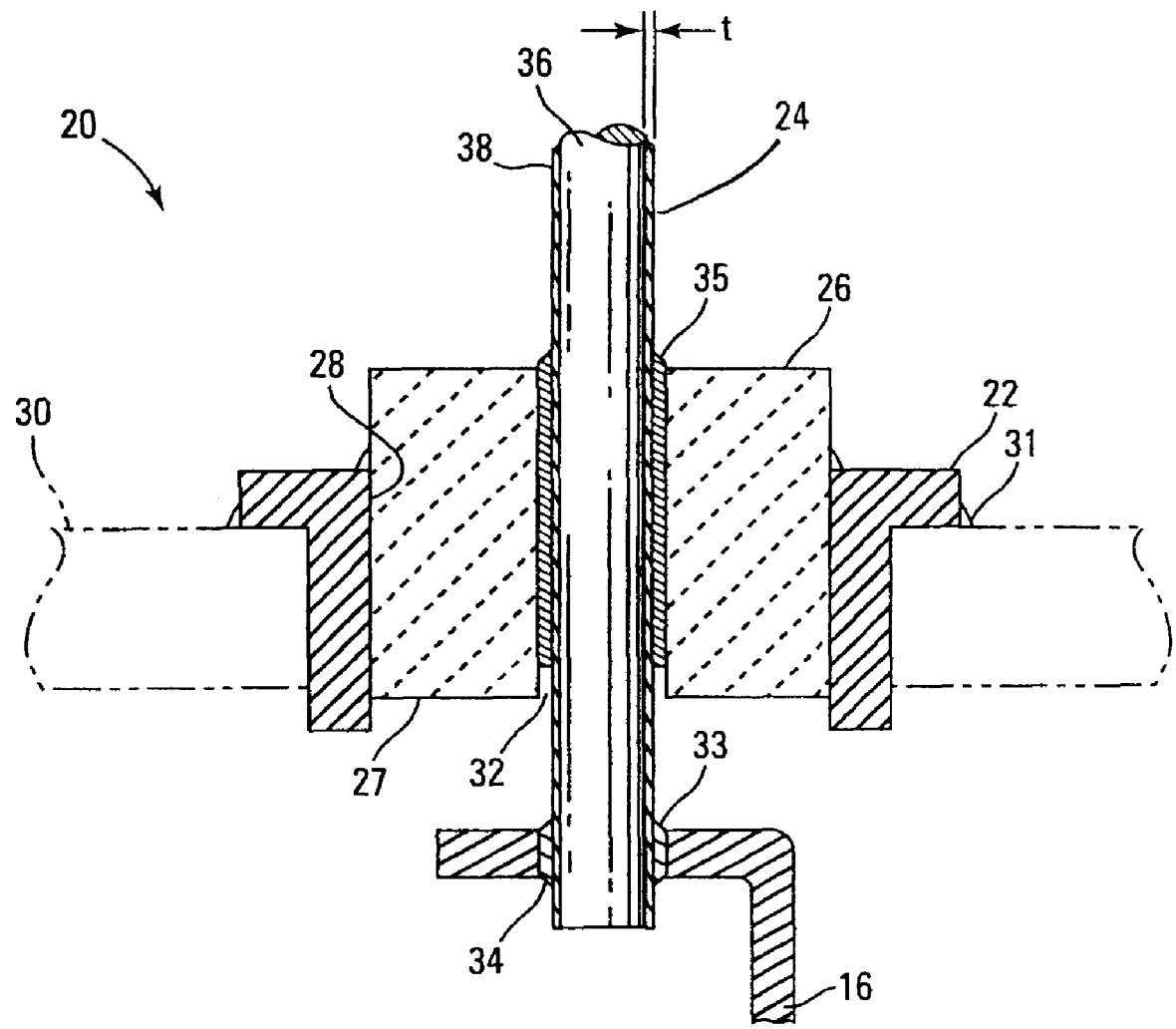
FIG. 3 is a partial cross-sectional view of an exemplary feedthrough, taken along the line 3-3 in FIG. 2, according to one embodiment of the present invention.

FIG. 3 shows a partial cross-sectional view of the feedthrough 20 electrically coupled to the PCB 16, according to one embodiment of the present invention. As shown in FIG. 3, the ferrule 22 is generally annular with an interior opening 27 and an interior wall 28, and may be constructed of an electrically conductive, biocompatible material, for example, titanium. The ferrule 22 is adapted to mate with a wall 30 of the housing 14. The ferrule 22 may be hermetically attached to the housing by a weld joint 31. The insulator 26 is partially disposed within the ferrule interior opening 27 and hermetically attached (e.g., by brazing) to the ferrule 22. In one embodiment, the insulator 26 consists of a metallized ceramic.

As depicted in FIG. 3, in one embodiment, the conductor 24 passes through an aperture 32 in the insulator 26. In one embodiment, the conductor 24 is sealed into the insulator 26 by a brazing operation as is known in the art. As depicted in FIG. 3, the braze material 35, which may consist of gold, hermetically seals the interior of the IMD housing. Inside the housing, the conductor 24 mates with the PCB 16. In one embodiment, the PCB 16 includes one or more ports 33. The port 33 is adapted to receive the conductor 24 and is electrically connected to corresponding PCB electronic circuitry. The electrical connection between the conductor 24 and IMD electrical device may be completed by effecting a solder joint 34 (e.g., a standard formulation of tin/lead solder) between the conductor 24 to an electrical trace surrounding the port 33. Alternatively, the conductor 24 may be soldered or welded to a conductive pad or terminal on the PCB 16.

As further shown in FIG. 3, the conductor 24 includes an inner wire or core 36 and an oxide-resistant coating 38. The core 36 may be made from any good electrically-conductive material, including, but not limited to tantalum, niobium, titanium, molybdenum, copper, or alloys of any of these metals. Although not a requirement, it may be beneficial to make the conductor 24 from biocompatible materials. According to such embodiments of the invention, the core 36 may consist of tantalum, niobium, titanium, or alloys of these metals. In one embodiment, the core 36 is made from a combination of tungsten and tantalum or a combination of zirconium and niobium, which can improve the mechanical fatigue characteristics of the core 36. The coating 38 can be applied by cladding or other coating processes known in the art, including electroplating and physical vapor deposition processes such as sputtering.

The oxide-resistant conductive coating 38 is applied to the core 36, as depicted in FIG. 3, to control oxide growth on the surface of the core 36. Conductors 24 consisting of only a tantalum- or niobium-based wire, without the coating 38, may not be readily soldered to the port 33 of the PCB 16, because the oxide layer would prevent the formation of an acceptable electrical connection. In various embodiments, the coating 38 may consist of oxide-resistant, electrically-conductive materials, including, but not limited to, gold, platinum, iridium, palladium, rhodium, ruthenium, titanium, and alloys thereof.

High temperature processes performed on the feedthrough during fabrication can adversely impact the solderability of the coated feedthrough conductor 24. One such exemplary process is a brazing process, which typically involves heating a portion of the feedthrough to an elevated temperature which in turn causes an increase in the temperature of the conductor 24. Such high temperature processes can adversely affect the solderability of the conductor 24, particularly where niobium, tantalum, or their alloys are used for the core 36, and where the coating 38 is not applied to a sufficient thickness. If the coating 38 has a sufficient thickness, however, the resulting conductor 24 can be readily soldered to the IMD electronic components. Thus, in one embodiment, the coating 38 is applied to a sufficient thickness to provide a solderable surface after the conductor 24 is sealed into the insulator 26 by brazing. In one embodiment, the coating 38 has a thickness, t, of at least about 2 microns, which results in a conductor 24 that can be effectively soldered. In another embodiment, the thickness, t, is from about 2 microns to about 50 microns. In another embodiment, the thickness, t, is about 20 microns.

Thus, exemplary embodiments of the feedthrough conductor 24 include a platinum or platinum-iridium clad coating 38 over a niobium or niobium-zirconium core 36. Other embodiments may include a platinum or platinum-iridium clad coating 38 over a tantalum or tantalum-tungsten core 36.

In other exemplary embodiments, the coating 38 includes platinum or platinum-iridium deposited on a tantalum, tantalum-tungsten, niobium, or niobium-zirconium core 36 by sputtering.

Figure 4:
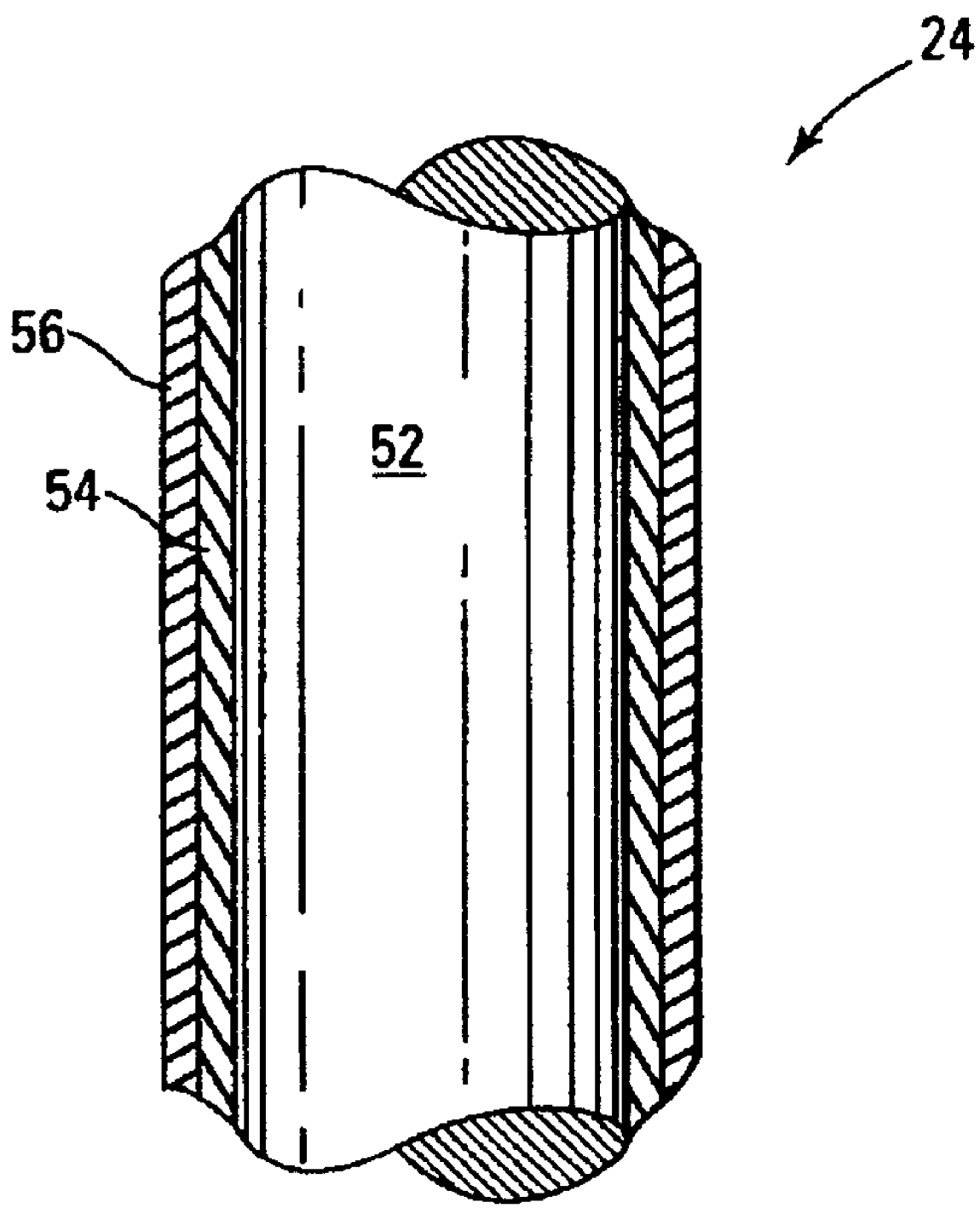
FIG. 4 is a cross-sectional view of an exemplary feedthrough conductor with multiple-layer coating over a solid conductor wire, for use in the feedthrough according to one embodiment of the present invention.

FIG. 4 shows another embodiment of a feedthrough conductor 24 for use in the feedthrough 20 of the present invention. As shown in FIG. 4, the conductor 24 includes an inner core 52, an intermediate coating layer 54, and an oxide-resistant outer coating layer 56. The outer coating layer 56 may consist of an electrically-conductive, oxide-resistant material such as gold, platinum, iridium, palladium, rhodium, ruthenium, and alloys thereof. The intermediate coating layer 54 provides a barrier layer between the outer coating layer 56 and intermetallics which may form at the interface between the core 52 and coating during the aforementioned high temperature processing, particularly when the core 52 is made from niobium or its alloys. The intermediate layer 54 deters these intermetallics from adversely impacting the fatigue strength of the conductor 24 and/or the hermeticity of the seal between the conductor 24 and the insulator 26. In one embodiment, the intermediate layer 54 is made from a relatively inexpensive, conductive material such as molybdenum. According to another embodiment, the conductor 24 consists of a niobium or niobium-zirconium core 52, a tantalum or tantalum-tungsten intermediate cladding layer 54, and a platinum or platinum-iridium outer cladding layer 56.

Figure 5:
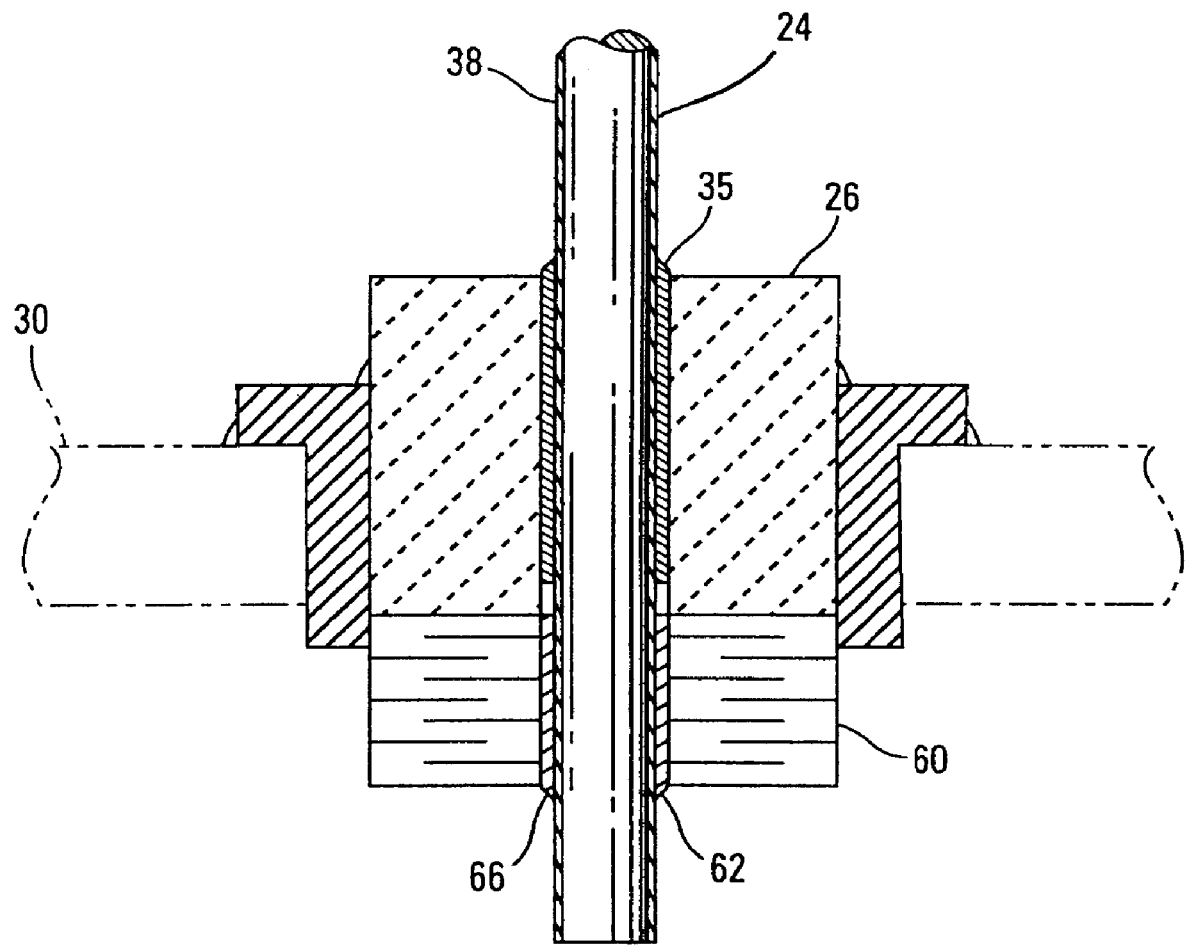
FIG. 5 is a partial cross-sectional view of an exemplary feedthrough employing an EMI filter capacitor, according to one embodiment of the present invention.

FIG. 5 shows partial cross-sectional view of an alternative embodiment of the feedthrough according to the current invention employing the coated conductor 24 and an EMI filter 60, which may consist of a capacitive structure as is well known in the art. The EMI filter 60 filters electromagnetic interference that could otherwise inhibit the performance of the IMD electronics inside the housing 14. As depicted in FIG. 5, in one embodiment, the conductor 24 extends through an aperture 62 in the EMI filter 60, which is disposed coaxially with the aperture 32 in the insulator 26. The conductor 24 is electrically connected to the EMI filter 60. In one embodiment, the electrical connection between the conductor 24 and the EMI filter 60 may be made by forming a solder joint 66, as shown in FIG. 5. In such an embodiment, the oxide-resistant coating 38, when applied to a sufficient thickness as discussed above, promotes a robust soldered electrical connection between the EMI filter 60 and the conductor 24. Alternatively, the EMI filter 60 and the conductor 24 may be electrically connected by other means, for example, by applying a metallized epoxy.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device for delivering a therapy, the device comprising:
    a hermetically-sealed housing enclosing an electronic component;
    a header coupled to the housing, the header adapted for receiving a terminal pin of a therapy lead; and
    a feedthrough coupled to the housing, the feedthrough comprising:
        a generally annular ferrule adapted to mate with an opening in the housing;
        an insulating material disposed within and coupled to the ferrule; and
        a coated conductor extending through the insulating material, the coated conductor including an inner core made substantially from tantalum, tantalum-tungsten alloy, niobium or niobium-zirconium alloy and an electrically conductive oxide-resistant coating made substantially of gold, platinum, iridium, palladium, rhodium, ruthenium, titanium or alloys thereof, the electrically conductive oxide-resistant coating being applied via cladding and having a thickness of at least 2.0 microns, wherein the coated conductor is configured to operatively couple the terminal pin of the therapy lead to the electronic component; and
        a layer of braze material coupling the coated conductor to the insulating material.

2. The device of claim 1 wherein the oxide-resistant coating has a thickness of at least 20 microns.

3. The device of claim 1 wherein the coated conductor further includes an intermediate layer between the inner core and the oxide-resistant coating.

4. The device of claim 1 further comprising a plurality of conductors each extending through the insulating material and including an inner core and an oxide-resistant coating having a thickness of at least 2.0 microns.

5. The device of claim 1 wherein the oxide-resistant coating is configured to render the coated conductor solderable to the electronic component.

6. The device of claim 1 wherein the insulating material includes a metallized ceramic material.

7. A feedthrough for use in an implantable medical device having a hermetically-sealed housing, a header coupled to the housing and adapted to receive a terminal pin of a therapy lead, and a printed circuit board located within the housing, the feedthrough comprising:
    a generally annular ferrule adapted to mate with an opening in the housing;
    an insulating material disposed within and coupled to the ferrule; and
    a conductor extending through the insulating material and having a proximal portion disposed within the header and a distal portion disposed within the housing, the conductor comprising an inner core and an oxide-resistant coating having a thickness of at least 2.0 microns, wherein the conductor is adapted to operatively couple the terminal pin of the therapy lead and the printed circuit board.

8. The feedthrough of claim 7 wherein the inner core is made substantially from tantalum, a tantalum alloy, niobium, or a niobium alloy.

9. The feedthrough of claim 8 wherein the oxide-resistant coating is made substantially of gold, platinum, iridium, palladium, rhodium, ruthenium, titanium, or alloys thereof.

10. The feedthrough of claim 9 further comprising a capacitive structure disposed within the housing and partially disposed within the ferrule, the capacitive structure being operatively coupled to the distal portion of the conductor.

11. The feedthrough of claim 9 wherein the oxide-resistant coating is configured to render the conductor distal portion solderable to the printed circuit board.

12. The feedthrough of claim 9 wherein the insulating material includes a metallized ceramic material.

13. The feedthrough of claim 9 wherein the conductor is hermetically attached to the insulating material by a braze material.

14. The feedthrough of claim 9 wherein the conductor includes an intermediate layer between the inner core and the oxide-resistant coating.

15. The feedthrough of claim 9 further comprising a plurality of conductors each extending though the insulating material and including an inner core and an oxide-resistant coating having a thickness of at least 2.0 microns.

* * * * *